(12) United States Patent
     Boesen

(10) Patent No.: US 12,574,669 B2
(45) Date of Patent: Mar. 10, 2026

(54) EARPIECE FOR AUDIOGRAMS

(71) Applicant: BRAGI GmbH, Munich (DE)

(72) Inventor: Peter Vincent Boesen, Munich (DE)

(73) Assignee: BRAGI GMBH, Munich (DE)

( * ) Notice: Subject to any disclaimer, the term of this patent is extended or adjusted under 35 U.S.C. 154(b) by 235 days.

(21) Appl. No.: 17/136,231

(22) Filed: Dec. 29, 2020

(65) Prior Publication Data

US 2021/0120326 A1     Apr. 22, 2021

Related U.S. Application Data

(63) Continuation of application No. 15/674,972, filed on Aug. 11, 2017, now Pat. No. 10,887,679.

(60) Provisional application No. 62/379,990, filed on Aug. 26, 2016.

(51) Int. Cl.
     *H04R 25/00*     (2006.01)
     *H04R 1/10*      (2006.01)
     *A61B 5/12*      (2006.01)
     *H04R 5/033*     (2006.01)

(52) U.S. Cl.
     CPC ............. *H04R 1/10* (2013.01); *H04R 1/1041* (2013.01); *A61B 5/12* (2013.01); *H04R 5/033* (2013.01); *H04R 25/70* (2013.01); *H04R 25/75* (2013.01); *H04R 2420/07* (2013.01); *H04R 2460/13* (2013.01)

(58) Field of Classification Search
     CPC ........ H04R 1/10; H04R 1/1041; H04R 5/033; H04R 25/70
     USPC .................................................. 381/74, 314
     See application file for complete search history.

(56) References Cited

U.S. PATENT DOCUMENTS

| | | | |
|---|---|---|---|
| 2,325,590 A | 7/1943 | Carlisle et al. | |
| 2,430,229 A | 11/1947 | Kelsey | |
| 3,047,089 A | 7/1962 | Zwislocki | |
| D208,784 S | 10/1967 | Sanzone | |
| 3,586,794 A | 6/1971 | Michaelis | |
| 3,934,100 A | 1/1976 | Harada | |
| 3,983,336 A | 9/1976 | Malek et al. | |

(Continued)

FOREIGN PATENT DOCUMENTS

| | | |
|---|---|---|
| CN | 204244472 U | 4/2015 |
| CN | 104837094 A | 8/2015 |

(Continued)

OTHER PUBLICATIONS

Akkermans, "Acoustic Ear Recognition for Person Identification", Automatic Identification Advanced Technologies, 2005 pp. 219-223.

(Continued)

*Primary Examiner* — Katherine A Faley
(74) *Attorney, Agent, or Firm* — Goodhue, Coleman & Owens, P.C.

(57) ABSTRACT

An earpiece is configured for providing audiometric testing. The earpiece includes an earpiece housing, an intelligent control system disposed within the earpiece housing, at least one transducer operatively connected to the intelligent control, and at least one speaker operatively connected to the intelligent control. The earpiece is configured to perform audiometric testing of a user by reproducing sounds at the at least one transducer and receiving user feedback regarding the sounds to provide audiometric test data.

12 Claims, 4 Drawing Sheets

(56) References Cited

U.S. PATENT DOCUMENTS

| | | | |
|---|---|---|---|
| 4,069,400 A | 1/1978 | Johanson et al. |
| 4,150,262 A | 4/1979 | Ono |
| 4,334,315 A | 6/1982 | Ono et al. |
| D266,271 S | 9/1982 | Johanson et al. |
| 4,375,016 A | 2/1983 | Harada |
| 4,588,867 A | 5/1986 | Konomi |
| 4,617,429 A | 10/1986 | Bellafiore |
| 4,654,883 A | 3/1987 | Iwata |
| 4,682,180 A | 7/1987 | Gans |
| 4,791,673 A | 12/1988 | Schreiber |
| 4,852,177 A | 7/1989 | Ambrose |
| 4,865,044 A | 9/1989 | Wallace et al. |
| 4,984,277 A | 1/1991 | Bisgaard et al. |
| 5,008,943 A | 4/1991 | Arndt et al. |
| 5,185,802 A | 2/1993 | Stanton |
| 5,191,602 A | 3/1993 | Regen et al. |
| 5,201,007 A | 4/1993 | Ward et al. |
| 5,201,008 A | 4/1993 | Arndt et al. |
| D340,286 S | 10/1993 | Seo |
| 5,280,524 A | 1/1994 | Norris |
| 5,295,193 A | 3/1994 | Ono |
| 5,298,692 A | 3/1994 | Ikeda et al. |
| 5,343,532 A | 8/1994 | Shugart |
| 5,347,584 A | 9/1994 | Narisawa |
| 5,363,444 A | 11/1994 | Norris |
| D367,113 S | 2/1996 | Weeks |
| 5,497,339 A | 3/1996 | Bernard |
| 5,606,621 A | 2/1997 | Reiter et al. |
| 5,613,222 A | 3/1997 | Guenther |
| 5,654,530 A | 8/1997 | Sauer et al. |
| 5,692,059 A | 11/1997 | Kruger |
| 5,721,783 A | 2/1998 | Anderson |
| 5,748,743 A | 5/1998 | Weeks |
| 5,749,072 A | 5/1998 | Mazurkiewicz et al. |
| 5,771,438 A | 6/1998 | Palermo et al. |
| D397,796 S | 9/1998 | Yabe et al. |
| 5,802,167 A | 9/1998 | Hong |
| D410,008 S | 5/1999 | Almqvist |
| 5,929,774 A | 7/1999 | Charlton |
| 5,933,506 A | 8/1999 | Aoki et al. |
| 5,949,896 A | 9/1999 | Nageno et al. |
| 5,987,146 A | 11/1999 | Pluvinage et al. |
| 6,021,207 A | 2/2000 | Puthuff et al. |
| 6,054,989 A | 4/2000 | Robertson et al. |
| 6,081,724 A | 6/2000 | Wilson |
| 6,084,526 A | 7/2000 | Blotky et al. |
| 6,094,492 A | 7/2000 | Boesen |
| 6,111,569 A | 8/2000 | Brusky et al. |
| 6,112,103 A | 8/2000 | Puthuff |
| 6,157,727 A | 12/2000 | Rueda |
| 6,167,039 A | 12/2000 | Karlsson et al. |
| 6,181,801 B1 | 1/2001 | Puthuff et al. |
| 6,208,372 B1 | 3/2001 | Barraclough |
| 6,230,029 B1 | 5/2001 | Yegiazaryan et al. |
| 6,275,789 B1 | 8/2001 | Moser et al. |
| 6,339,754 B1 | 1/2002 | Flanagan et al. |
| D455,835 S | 4/2002 | Anderson et al. |
| 6,408,081 B1 | 6/2002 | Boesen |
| 6,424,820 B1 | 7/2002 | Burdick et al. |
| D464,039 S | 10/2002 | Boesen |
| 6,470,893 B1 | 10/2002 | Boesen |
| D468,299 S | 1/2003 | Boesen |
| D468,300 S | 1/2003 | Boesen |
| 6,542,721 B2 | 4/2003 | Boesen |
| 6,560,468 B1 | 5/2003 | Boesen |
| 6,654,721 B2 | 11/2003 | Handelman |
| 6,664,713 B2 | 12/2003 | Boesen |
| 6,690,807 B1 | 2/2004 | Meyer |
| 6,694,180 B1 | 2/2004 | Boesen |
| 6,718,043 B1 | 4/2004 | Boesen |
| 6,738,485 B1 | 5/2004 | Boesen |
| 6,748,095 B1 | 6/2004 | Goss |
| 6,754,358 B1 | 6/2004 | Boesen et al. |
| 6,784,873 B1 | 8/2004 | Boesen et al. |
| 6,823,195 B1 | 11/2004 | Boesen |

| | | | |
|---|---|---|---|
| 6,852,084 B1 | 2/2005 | Boesen |
| 6,879,698 B2 | 4/2005 | Boesen |
| 6,892,082 B2 | 5/2005 | Boesen |
| 6,920,229 B2 | 7/2005 | Boesen |
| 6,952,483 B2 | 10/2005 | Boesen et al. |
| 6,987,986 B2 | 1/2006 | Boesen |
| 7,010,137 B1 | 3/2006 | Leedom et al. |
| 7,113,611 B2 | 9/2006 | Leedom et al. |
| D532,520 S | 11/2006 | Kampmeier et al. |
| 7,136,282 B1 | 11/2006 | Rebeske |
| 7,203,331 B2 | 4/2007 | Boesen |
| 7,209,569 B2 | 4/2007 | Boesen |
| 7,215,790 B2 | 5/2007 | Boesen et al. |
| D549,222 S | 8/2007 | Huang |
| D554,756 S | 11/2007 | Sjursen et al. |
| 7,403,629 B1 | 7/2008 | Aceti et al. |
| D579,006 S | 10/2008 | Kim et al. |
| 7,463,902 B2 | 12/2008 | Boesen |
| 7,508,411 B2 | 3/2009 | Boesen |
| D601,134 S | 9/2009 | Elabidi et al. |
| 7,825,626 B2 | 11/2010 | Kozisek |
| 7,965,855 B1 | 6/2011 | Ham |
| 7,979,035 B2 | 7/2011 | Griffin et al. |
| 7,983,628 B2 | 7/2011 | Boesen |
| D647,491 S | 10/2011 | Chen et al. |
| 8,095,188 B2 | 1/2012 | Shi |
| 8,108,143 B1 | 1/2012 | Tester |
| 8,140,357 B1 | 3/2012 | Boesen |
| D666,581 S | 9/2012 | Perez |
| 8,300,864 B2 | 10/2012 | Müllenborn et al. |
| 8,406,448 B2 | 3/2013 | Lin et al. |
| 8,436,780 B2 | 5/2013 | Schantz et al. |
| D687,021 S | 7/2013 | Yuen |
| 8,494,507 B1* | 7/2013 | Tedesco ................. G09B 21/00 |
| | | | 455/418 |
| 8,719,877 B2 | 5/2014 | VonDoenhoff et al. |
| 8,774,434 B2 | 7/2014 | Zhao et al. |
| 8,831,266 B1 | 9/2014 | Huang |
| 8,891,800 B1 | 11/2014 | Shaffer |
| 8,994,498 B2 | 3/2015 | Agrafioti et al. |
| D728,107 S | 4/2015 | Martin et al. |
| 9,013,145 B2 | 4/2015 | Castillo et al. |
| 9,037,125 B1 | 5/2015 | Kadous |
| D733,103 S | 6/2015 | Jeong et al. |
| 9,081,944 B2 | 7/2015 | Camacho et al. |
| 9,497,530 B1* | 11/2016 | Campbell ............ H04R 1/1091 |
| 9,510,159 B1 | 11/2016 | Cuddihy et al. |
| D773,439 S | 12/2016 | Walker |
| D775,158 S | 12/2016 | Dong et al. |
| D777,710 S | 1/2017 | Palmborg et al. |
| D788,079 S | 5/2017 | Son et al. |
| 2001/0005197 A1 | 6/2001 | Mishra et al. |
| 2001/0027121 A1 | 10/2001 | Boesen |
| 2001/0043707 A1 | 11/2001 | Leedom |
| 2001/0056350 A1 | 12/2001 | Calderone et al. |
| 2002/0002413 A1 | 1/2002 | Tokue |
| 2002/0007510 A1 | 1/2002 | Mann |
| 2002/0010590 A1 | 1/2002 | Lee |
| 2002/0030637 A1 | 3/2002 | Mann |
| 2002/0046035 A1 | 4/2002 | Kitahara et al. |
| 2002/0057810 A1 | 5/2002 | Boesen |
| 2002/0076073 A1 | 6/2002 | Taenzer et al. |
| 2002/0118852 A1 | 8/2002 | Boesen |
| 2002/0196955 A1* | 12/2002 | Boesen ................... H04M 1/05 |
| | | | 381/326 |
| 2003/0002705 A1 | 1/2003 | Boesen |
| 2003/0065504 A1 | 4/2003 | Kraemer et al. |
| 2003/0100331 A1 | 5/2003 | Dress et al. |
| 2003/0104806 A1 | 6/2003 | Ruef et al. |
| 2003/0115068 A1 | 6/2003 | Boesen |
| 2003/0125096 A1 | 7/2003 | Boesen |
| 2003/0218064 A1 | 11/2003 | Conner et al. |
| 2004/0070564 A1 | 4/2004 | Dawson et al. |
| 2004/0073136 A1* | 4/2004 | Thornton ............... A61B 5/742 |
| | | | 600/559 |
| 2004/0160511 A1 | 8/2004 | Boesen |
| 2005/0017842 A1 | 1/2005 | Dematteo |
| 2005/0043056 A1 | 2/2005 | Boesen |
| 2005/0094839 A1 | 5/2005 | Gwee |

(56) References Cited

U.S. PATENT DOCUMENTS

| 2005/0125320 A1 | 6/2005 | Boesen |
| 2005/0148883 A1 | 7/2005 | Boesen |
| 2005/0165663 A1 | 7/2005 | Razumov |
| 2005/0196009 A1 | 9/2005 | Boesen |
| 2005/0251455 A1 | 11/2005 | Boesen |
| 2005/0266876 A1 | 12/2005 | Boesen |
| 2006/0014570 A1* | 1/2006 | Marx ..................... H04R 5/04 |
| | | 455/569.1 |
| 2006/0029246 A1 | 2/2006 | Boesen |
| 2006/0073787 A1 | 4/2006 | Lair et al. |
| 2006/0074671 A1 | 4/2006 | Farmaner et al. |
| 2006/0074808 A1 | 4/2006 | Boesen |
| 2006/0094981 A1* | 5/2006 | Camp .................... H04R 25/70 |
| | | 600/559 |
| 2006/0166715 A1 | 7/2006 | Engelen et al. |
| 2006/0166716 A1 | 7/2006 | Seshadri et al. |
| 2006/0220915 A1 | 10/2006 | Bauer |
| 2006/0222194 A1* | 10/2006 | Bramslow ............. H04R 25/70 |
| | | 381/314 |
| 2006/0258412 A1 | 11/2006 | Liu |
| 2007/0071263 A1* | 3/2007 | Beck ..................... H04R 5/04 |
| | | 381/315 |
| 2008/0076972 A1 | 3/2008 | Dorogusker et al. |
| 2008/0090622 A1 | 4/2008 | Kim et al. |
| 2008/0137873 A1* | 6/2008 | Goldstein ........... H04R 1/1083 |
| | | 381/57 |
| 2008/0146890 A1 | 6/2008 | LeBoeuf et al. |
| 2008/0226103 A1* | 9/2008 | Schobben ............... H04R 5/04 |
| | | 381/309 |
| 2008/0254780 A1 | 10/2008 | Kuhl et al. |
| 2008/0255430 A1 | 10/2008 | Alexandersson et al. |
| 2008/0267433 A1 | 10/2008 | Katou et al. |
| 2009/0003620 A1 | 1/2009 | McKillop et al. |
| 2009/0008275 A1 | 1/2009 | Ferrari et al. |
| 2009/0017881 A1 | 1/2009 | Madrigal |
| 2009/0073070 A1 | 3/2009 | Rofougaran |
| 2009/0097689 A1 | 4/2009 | Prest et al. |
| 2009/0105548 A1 | 4/2009 | Bart |
| 2009/0191920 A1 | 7/2009 | Regen et al. |
| 2009/0245559 A1 | 10/2009 | Boltyenkov et al. |
| 2009/0261114 A1 | 10/2009 | McGuire et al. |
| 2009/0296968 A1 | 12/2009 | Wu et al. |
| 2010/0033313 A1 | 2/2010 | Keady et al. |
| 2010/0203831 A1 | 8/2010 | Muth |
| 2010/0210212 A1 | 8/2010 | Sato |
| 2010/0320961 A1 | 12/2010 | Castillo et al. |
| 2011/0140844 A1 | 6/2011 | McGuire et al. |
| 2011/0239497 A1 | 10/2011 | McGuire et al. |
| 2011/0286615 A1 | 11/2011 | Olodort et al. |
| 2012/0057740 A1 | 3/2012 | Rosal |
| 2012/0288119 A1 | 11/2012 | Apfel |
| 2012/0290297 A1* | 11/2012 | Baughman .............. G10L 17/22 |
| | | 704/E15.039 |
| 2013/0094659 A1 | 4/2013 | Liu |
| 2013/0316642 A1* | 11/2013 | Newham ........... H04W 52/0206 |
| | | 455/67.11 |
| 2013/0346168 A1 | 12/2013 | Zhou et al. |
| 2014/0079257 A1 | 3/2014 | Ruwe et al. |
| 2014/0106677 A1 | 4/2014 | Altman |
| 2014/0122116 A1 | 5/2014 | Smythe |
| 2014/0153768 A1 | 6/2014 | Hagen et al. |
| 2014/0163771 A1 | 6/2014 | Demeniuk |
| 2014/0185828 A1 | 7/2014 | Helbling |
| 2014/0219467 A1 | 8/2014 | Kurtz |
| 2014/0222462 A1 | 8/2014 | Shakil et al. |
| 2014/0235169 A1 | 8/2014 | Parkinson et al. |
| 2014/0270227 A1 | 9/2014 | Swanson |
| 2014/0270271 A1 | 9/2014 | Dehe et al. |
| 2014/0314261 A1* | 10/2014 | Selig .................... A61B 5/6898 |
| | | 381/314 |
| 2014/0335908 A1 | 11/2014 | Krisch et al. |
| 2014/0348367 A1 | 11/2014 | Vavrus et al. |
| 2015/0028996 A1 | 1/2015 | Agrafioti et al. |
| 2015/0110587 A1 | 4/2015 | Hori |
| 2015/0148989 A1 | 5/2015 | Cooper et al. |
| 2015/0172770 A1 | 6/2015 | Kim et al. |
| 2015/0179189 A1 | 6/2015 | Dadu et al. |
| 2015/0245127 A1 | 8/2015 | Shaffer |
| 2015/0358745 A1* | 12/2015 | Rix ........................ G10K 11/16 |
| | | 381/60 |
| 2016/0008176 A1* | 1/2016 | Goldstein ............... A61F 11/10 |
| | | 128/864 |
| 2016/0033280 A1 | 2/2016 | Moore et al. |
| 2016/0072558 A1 | 3/2016 | Hirsch et al. |
| 2016/0073189 A1 | 3/2016 | Lindén et al. |
| 2016/0125892 A1 | 5/2016 | Bowen et al. |
| 2016/0360350 A1 | 12/2016 | Watson et al. |
| 2017/0059152 A1 | 3/2017 | Hirsch et al. |
| 2017/0060262 A1 | 3/2017 | Hviid et al. |
| 2017/0060269 A1 | 3/2017 | Förstner et al. |
| 2017/0061751 A1 | 3/2017 | Loermann et al. |
| 2017/0062913 A1 | 3/2017 | Hirsch et al. |
| 2017/0064426 A1 | 3/2017 | Hviid |
| 2017/0064428 A1 | 3/2017 | Hirsch |
| 2017/0064432 A1 | 3/2017 | Hviid et al. |
| 2017/0064437 A1 | 3/2017 | Hviid et al. |
| 2017/0078780 A1 | 3/2017 | Qian et al. |
| 2017/0108918 A1 | 4/2017 | Boesen |
| 2017/0109131 A1 | 4/2017 | Boesen |
| 2017/0110124 A1 | 4/2017 | Boesen et al. |
| 2017/0110899 A1 | 4/2017 | Boesen |
| 2017/0111723 A1 | 4/2017 | Boesen |
| 2017/0111725 A1 | 4/2017 | Boesen et al. |
| 2017/0111726 A1 | 4/2017 | Martin et al. |
| 2017/0111740 A1 | 4/2017 | Hviid et al. |
| 2017/0151447 A1 | 6/2017 | Boesen |
| 2017/0151668 A1 | 6/2017 | Boesen |
| 2017/0151918 A1 | 6/2017 | Boesen |
| 2017/0151930 A1 | 6/2017 | Boesen |
| 2017/0151957 A1 | 6/2017 | Boesen |
| 2017/0151959 A1 | 6/2017 | Boesen |
| 2017/0153114 A1 | 6/2017 | Boesen |
| 2017/0153636 A1 | 6/2017 | Boesen |
| 2017/0154532 A1 | 6/2017 | Boesen |
| 2017/0155985 A1 | 6/2017 | Boesen |
| 2017/0155992 A1 | 6/2017 | Perianu et al. |
| 2017/0155993 A1 | 6/2017 | Boesen |
| 2017/0155997 A1 | 6/2017 | Boesen |
| 2017/0155998 A1 | 6/2017 | Boesen |
| 2017/0156000 A1 | 6/2017 | Boesen |
| 2017/0178631 A1 | 6/2017 | Boesen |
| 2017/0180842 A1 | 6/2017 | Boesen |
| 2017/0180843 A1 | 6/2017 | Perianu et al. |
| 2017/0180897 A1 | 6/2017 | Perianu |
| 2017/0188127 A1 | 6/2017 | Perianu et al. |
| 2017/0188132 A1 | 6/2017 | Hirsch et al. |
| 2017/0195829 A1 | 7/2017 | Belverato et al. |
| 2017/0208393 A1 | 7/2017 | Boesen |
| 2017/0214987 A1 | 7/2017 | Boesen |
| 2017/0215016 A1 | 7/2017 | Dohmen et al. |
| 2017/0230752 A1 | 8/2017 | Dohmen et al. |
| 2017/0257698 A1 | 9/2017 | Boesen et al. |
| 2017/0318457 A1* | 11/2017 | Westermann .......... G16H 40/67 |

FOREIGN PATENT DOCUMENTS

| EP | 1469659 A1 | 10/2004 |
| EP | 1017252 A3 | 5/2006 |
| EP | 2903186 A1 | 8/2015 |
| GB | 2074817 | 11/1981 |
| GB | 2508226 A | 5/2014 |
| WO | 2008103925 A1 | 8/2008 |
| WO | 2007034371 A3 | 11/2008 |
| WO | 2011001433 A2 | 1/2011 |
| WO | 2012071127 A1 | 5/2012 |
| WO | 2013134956 A1 | 9/2013 |
| WO | 2014046602 A1 | 3/2014 |
| WO | 2014043179 A3 | 7/2014 |
| WO | 2015061633 A2 | 4/2015 |
| WO | 2015110577 A1 | 7/2015 |

(56)        References Cited

FOREIGN PATENT DOCUMENTS

WO      2015110587 A1    7/2015
WO      2016032990 A1    3/2016

OTHER PUBLICATIONS

Announcing the $3,333,333 Stretch Goal (Feb. 24, 2014) pp. 1-14.
Ben Coxworth: "Graphene-based ink could enable low-cost, foldable electronics", "Journal of Physical Chemistry Letters", Northwestern University, (May 22, 2013), pp. 1-7.
Blain: "World's first graphene speaker already superior to Sennheiser MX400", htt://www.gizmag.com/graphene-speaker-beats-sennheiser-mx400/31660, (Apr. 15, 2014).
BMW, "BMW introduces BMW Connected—The personalized digital assistant", "http://bmwblog.com/2016/01/05/bmw-introduces-bmw-connected-the-personalized-digital-assistant", (Jan. 5, 2016).
Bragi is on Facebook (2014), pp. 1-51.
Bragi Update—Arrival of Prototype Chassis Parts—More People—Awesomeness (May 13, 2014), pp. 1-8.
Bragi Update—Chinese New Year, Design Verification, Charging Case, More People, Timeline(Mar. 6, 2015), pp. 1-18.
Bragi Update—First Sleeves From Prototype Tool—Software Development Kit (Jun. 5, 2014), pp. 1-8.
Bragi Update—Let's Get Ready ro Rumble, a Lot to be Done Over Christmas (Dec. 22, 2014), pp. 1-18.
Bragi Update—Memories From April—Update on Progress (Sep. 16, 2014), pp. 1-15.
Bragi Update—Memories from May—Update on Progress—Sweet (Oct. 13, 2014), pp. 1-16.
Bragi Update—Memories From One Month Before Kickstarter—Update on Progress (Jul. 10, 2014), pp. 1-17.
Bragi Update—Memories From The First Month of Kickstarter—Update on Progress (Aug. 1, 2014), pp. 1-16.
Bragi Update—Memories From The Second Month of Kickstarter—Update on Progress (Aug. 22, 2014), pp. 1-15.
Bragi Update—New People @Bragi—Prototypes (Jun. 26, 2014), pp. 1-9.
Bragi Update—Office Tour, Tour to China, Tour to CES (Dec. 11, 2014), pp. 1-14.
Bragi Update—Status on Wireless, Bits and Pieces, Testing—Oh Yeah, Timeline(Apr. 24, 2015), pp. 1-18.
Bragi Update—The App Preview, The Charger, The SDK, Bragi Funding and Chinese New Year (Feb. 11, 2015), pp. 1-19.
Bragi Update—What We Did Over Christmas, Las Vegas & CES (Jan. 19, 2014), pp. 1-21.
Bragi Update—Years of Development, Moments of Utter Joy and Finishing What we Started(Jun. 5, 2015), pp. 1-21.
Bragi Update—Alpha 5 and Back to China, Backer Day, on Track(May 16, 2015), pp. 1-15.
Bragi Update—Beta2 Production and Factory Line(Aug. 20, 2015), pp. 1-16.

Bragi Update—Certifications, Production, Ramping Up (Nov. 13, 2015), pp. 1-15.
Bragi Update—Developer Units Shipping and Status(Oct. 5, 2015), pp. 1-20.
Bragi Update—Developer Units Started Shipping and Status (Oct. 19, 2015), pp. 1-20.
Bragi Update—Developer Units, Investment, Story and Status(Nov. 2, 2015), pp. 1-14.
Bragi Update—Getting Close(Aug. 6, 2015), pp. 1-20.
Bragi Update—On Track, Design Verification, How it Works and What's Next(Jul. 15, 2015), pp. 1-17.
Bragi Update—On Track, on Track and Gems Overview (Jun. 24, 2015), pp. 1-19.
Bragi Update—Status on Wireless, Supply, Timeline and Open House@BRAGI(Apr. 1, 2015), pp. 1-17.
Bragi Update—Unpacking Video, Reviews on Audio Perform and Boy are we Getting Close(Sep. 10, 2015), pp. 1-15.
Healthcare Risk Management Review, "Nuance updates computer-assisted physician documentation solution" (Oct. 20, 2016), pp. 1-2.
Hoyt et al., "Lessons Learned from Implementation of Voice Recognition for Documentation in the Military Electronic Health Record System", The American Health Information Management Association (2017), pp. 1-8.
Hyundai Motor America, "Hyundai Motor Company Introduces A Health + Mobility Concept for Wellness in Mobility", Fountain Valley, Californa (2017), pp. 1-3.
International Search Report & Written Opinion, PCT/EP2016/070231 (Nov. 18, 2016).
Last Push Before The Kickstarter Campaign Ends on Monday 4pm CET (Mar. 28, 2014), pp. 1-7.
Nigel Whitfield: "Fake tape detectors, 'from the stands' footie and UGH? Internet of Things in my set-top box"; http://www.theregister.co.uk/2014/09/24/ibc_round_up_object_audio_dlna_iot/ (Sep. 24, 2014).
Staab, Wayne J., et al., "A One-Size Disposable Hearing Aid is Introduced", The Hearing Journal 53(4):36-41) Apr. 2000.
Stretchgoal—It's Your Dash (Feb. 14, 2014), pp. 1-14.
Stretchgoal—The Carrying Case for The Dash (Feb. 12, 2014), pp. 1-9.
Stretchgoal—Windows Phone Support (Feb. 17, 2014), pp. 1-17.
The Dash + The Charging Case & The Bragi News (Feb. 21, 2014), pp. 1-12.
The Dash—A Word From Our Software, Mechanical and Acoustics Team + An Update (Mar. 11, 2014), pp. 1-7.
Update From Bragi—$3,000,000—Yipee (Mar. 22, 2014), pp. 1-11.
Wikipedia, "Gamebook", https://en.wikipedia.org/wiki/Gamebook, Sep. 3, 2017, 5 pages.
Wikipedia, "Kinect", "https://en.wikipedia.org/wiki/Kinect", 18 pages, (Sep. 9, 2017).
Wikipedia, "Wii Balance Board", "https://en.wikipedia.org/wiki/Wii_Balance_Board", 3 pages, (Jul. 20, 2017).

* cited by examiner

EARPIECE FOR AUDIOGRAMS

PRIORITY STATEMENT

This application is continuation of U.S. Non-Provisional patent application Ser. No. 15/674,972, filed Aug. 11, 2017 which claims priority to U.S. Provisional Patent Application 62/379,990, filed on Aug. 26, 2016, and both entitled Earpiece for audiograms, hereby incorporated by reference in their entirety.

FIELD OF THE INVENTION

The present invention relates to earpieces. More particularly, but not exclusively, the present invention relates to earpieces configured to perform audiograms.

BACKGROUND

Audiograms are a commonly used diagnostic tool in audiology. Essentially, an audiogram is a graph that illustrates an audible threshold for different standardized frequencies. Typically, the x axis represents frequency (commonly measured in Hertz) and y axis represents intensity (commonly measured in decibel) (dB). The threshold may then be plotted against a standardized curve associated with normal hearing. The testing to perform an audiogram is performed using specialized equipment known as an audiometer.

Results of an audiogram may be interpreted by a trained professional and used to select or configure a hearing aid for the individual. For example, based on the results of an audiogram, hearing loss may be characterized as conductive hearing loss, sensorineural hearing loss, noise damage, age-related hearing loss, or other types of hearing loss. Additional testing of other types may be indicated based on the results of an audiogram and in some cases type of hearing loss may suggest a particular medical intervention. Despite the recognized value of audiograms and their common use, problems remain.

For example, audiograms are expensive and time consuming. One has to set up an appointment, wait in the waiting room and be seen by a person (or for Otogram, be placed in the chair and given instructions as to what to do do), and wait for the interpretation. Moreover, one may end up being sold a hearing aid that does not adequately address the individual's needs fully and completely. Of course, these specialized services and use specialized equipment such as the audiometer, require a professional's time, and ultimately results in individuals (or their insurers) paying a premium.

Therefore, what is needed is a revolutionary and radically different approach.

SUMMARY

Therefore, it is a primary object, feature, or advantage of the present invention to improve over the state of the art.

It is a further object, feature, or advantage of the present invention to provide an earpiece which is configured for performing audiometric testing.

It is a still further object, feature, or advantage to customize audio reproduced for a user of a wireless earpiece based on results of audiometric testing of the user, the audiometric testing performed by the wireless earpiece.

One or more of these and/or other objects, features, or advantages of the present invention will become apparent from the specification and claims that follow. No single embodiment need provide each and every object, feature, or advantage. Different embodiments may have different objects, features, or advantages. Therefore, the present invention is not to be limited to or by an objects, features, or advantages stated herein.

According to one aspect, an earpiece is configured for providing audiometric testing. The earpiece includes an earpiece housing, an intelligent control system disposed within the earpiece housing, at least one transducer operatively connected to the intelligent control, and at least one speaker operatively connected to the intelligent control. The earpiece is configured to perform audiometric testing of a user by reproducing sounds at the at least one transducer and receiving user feedback regarding the sounds to provide audiometric test data. The audiometric test data may include frequency data and intensity data. The earpiece may further include a wireless transceiver operatively connected to the intelligent control system and wherein the earpiece is configured to communicate the audiometric test data to a remote device using the wireless transceiver. The at least one transducer may include an air conduction microphone, a bone conduction microphone or both. The at least one transducer may include a bone conduction transducer which is configured to operate as a bone conduction microphone in a first mode of operation and to generate vibrations in a second mode of operation. The audiometric testing may provide for reproducing the sounds using the bone conduction transduction in the second mode of operation and the air conduction microphone. The earpiece may be a first earpiece in a set of earpieces including the first earpiece for a first ear and a second earpiece for a second ear and wherein the first earpiece is configured to mask sounds at the first ear during audiometric testing of the second ear with the second earpiece. The user feedback may be voice feedback. The earpiece may include a gestural interface operatively connected to the intelligent control system and the user feedback may be gestural feedback performed through the gestural interface. The earpiece may further include at least one inertial sensor operatively connected to the intelligent control system and the user feedback may include user movement detected using the at one inertial sensor. The audiometric testing may include a pure tone test and/or a speech test. The earpiece may be further configured to adjust one or more audio settings associated with the earpiece based on the audiometric test data. The audiometric testing may include tinnitus frequency matching.

According to another aspect, a set of earpieces configured for audiometric testing. The set of earpieces includes a left earpiece and a right earpiece wherein each of the left earpiece and the right earpiece comprise an earpiece housing, an intelligent control system disposed within the earpiece housing, at least one transducer operatively connected to the intelligent control, and at least one speaker operatively connected to the intelligent control. The set of earpieces is configured to perform audiometric testing of a user by reproducing sounds at the at least one transducer of the left earpiece and/or the right earpiece and receiving user feedback regarding the sounds to provide audiometric test data. The audiometric test may include frequency data and intensity data. Each of the left earpiece and the right earpiece may further include a wireless transceiver operatively connected to the intelligent control system and the earpiece may be configured to communicate the audiometric test data to a remote device using the wireless transceiver. Each of the left earpiece and the right earpiece may include an air conduction microphone and a bone conduction microphone. A bone conduction transducer may be configured to operate as a bone conduction microphone in a first mode of operation and to generate vibrations in a second mode of operation. In the second mode of operation, the audiometric testing may provide for reproducing the sounds using the bone conduction and an air conduction microphone. The left earpiece may be configured to mask sounds at a left ear during audiometric testing of a right ear with the right earpiece and wherein the right earpiece is configured to mask sounds at a right ear during audiometric testing of the left ear with the left earpiece.

According to another aspect, a method for performing audiometric testing is provided. The method includes steps of generating a sound at a speaker of a wireless earpiece, receiving feedback from a person under test at the wireless earpiece, and generating audiometric data characterizing hearing of the person based on characteristics of the sound and the feedback, wherein the generating the audiometric data is performed by the wireless earpiece. The wireless earpiece may include at least one microphone and the feedback from the person under test may be voice input from the person under test. The wireless earpiece may include a gestural interface and the feedback from the person under test may include at least one gesture. The wireless earpiece may include at least one inertial sensor and the feedback from the person under test may include movement detectable with the at least one inertial sensor. The sound may be a pure tone sound and the audiometric data may be pure tone test data. The sound may be associated with speech testing. Contemporaneously with generating the sound at a left earpiece, the method may include generating a masking sound at a right earpiece. The sound may match a tinnitus frequency. The method may further include modifying an audio signal at the wireless earpiece using the audio profile of the user to provide a modified audio signal and transducing the modified audio signal at the earpiece.

According to another aspect the testing may be performed for unilateral right, unilateral left, bilateral left and right evaluations for possible hearing loss.

According to another aspect, a set of earpieces is configured for audiometric testing. The set includes a left earpiece and a right earpiece wherein each of the left earpiece and the right earpiece comprise an earpiece housing, an intelligent control system disposed within the earpiece housing, at least one transducer operatively connected to the intelligent control, and at least one speaker operatively connected to the intelligent control. The set of earpieces is configured to perform audiometric testing of a user by reproducing sounds at least one of the at least one transducer of the left earpiece and at least one transducer of the right earpiece and receiving user feedback regarding the sounds to provide audiometric test data at the set of earpieces, wherein the audiometric test data comprises frequency data and intensity data.

DETAILED DESCRIPTION

The present invention provides one or a set of earpieces which are capable of performing audiometric testing including producing audiogram data associated with hearing tests and related methods and systems.

Figure 1:
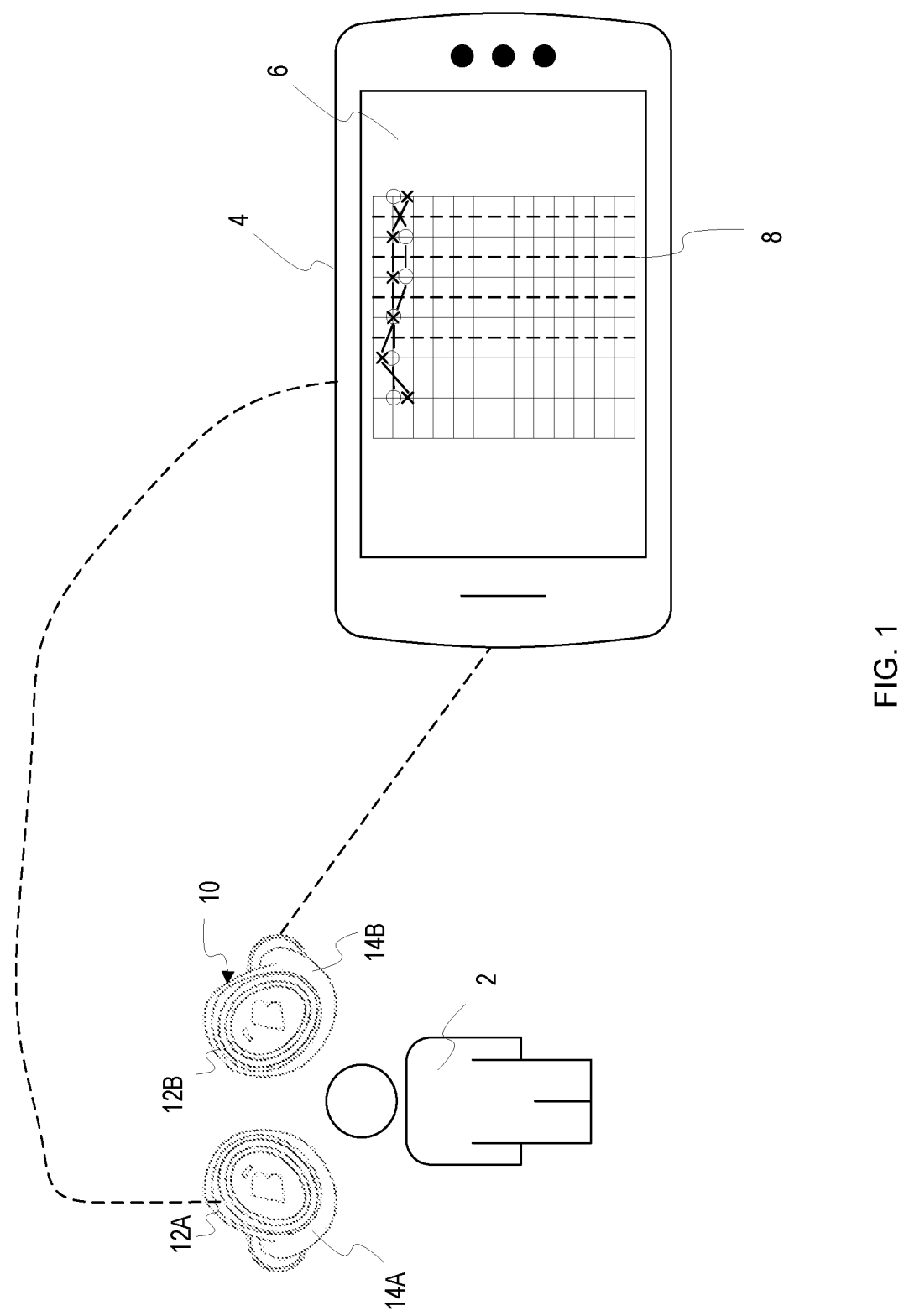
FIG. 1 illustrates a system with a pair of earpieces configured to do audiometric testing and showing results of the audiometric testing on an audiogram on a mobile device.

FIG. 1 illustrates an overview of one example of a system and method. As shown in FIG. 1, a pair of wireless earpieces 10 are shown which includes a left earpiece 12A with a left earpiece housing 14A and a right earpiece 12B with a right earpiece housing 14B. The earpieces may be worn by a person 2 in order to test the hearing of the person 2. Hearing tests may be administered by one or both of the earpieces 12A, 12B. Results of the hearing tests may be conveyed to another computing device such as a device having a display associated with it. As shown in FIG. 1, a mobile device 4 has a display 6 on which is shown one example of an audiogram 8 based on test results received from one or more of the earpieces 12A, 12B. The audiogram shown provides frequency levels across the x-axis and hearing levels in decibel (dB) along the y-axis. Note that instead of decibel, decibel Hearing Level (dBHL) may be used. DBHL units are not absolute intensity levels but instead represent a variance between a measured hearing level and a normal hearing level. Of course, any number of other types of audiograms may be displayed.

Figure 2:
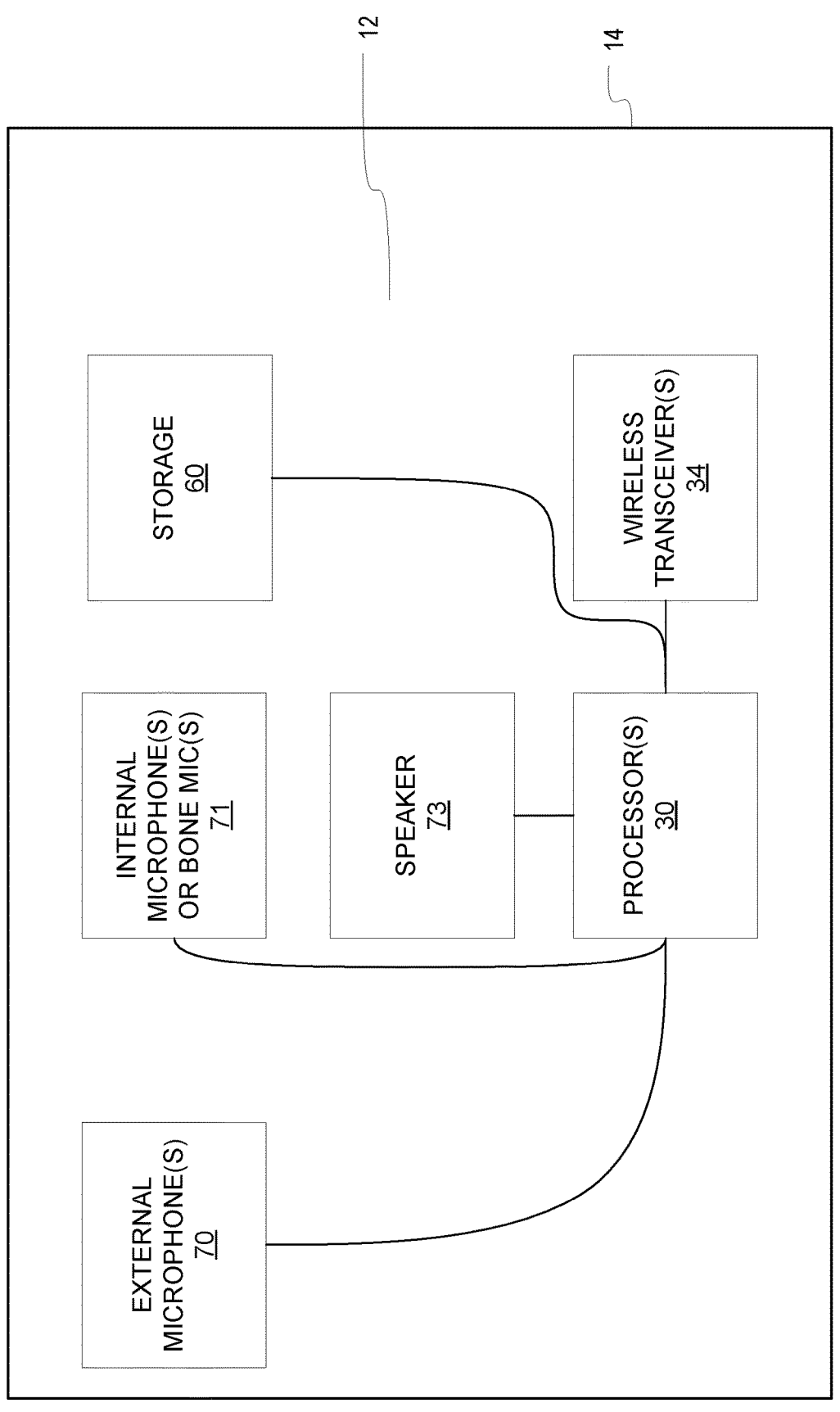
FIG. 2 illustrates a block diagram of one example of an earpiece configured for audiometric testing.

FIG. 2 illustrates a block diagram of one example of an earpiece 12 in more detail. The earpiece 12 has an earpiece housing 14. An intelligent control system including one or more processors 30 may be present within the earpiece housing 14. An external microphone 70 may be operatively connected to the one or more processors 30. One or more internal microphones or bone microphones 71 may also be operatively connected to the processor 30. A speaker 73 is also operatively connected to the one or more processors 30. The microphones 70, 71 and speaker 73 may be used in administering various audiometric testing as will be explained in more detail later herein. Onboard storage 60 may also be operatively connected to the one or more processors as well. The onboard storage 60 may store audio files used for pure tone testing or alternatively, the tones for pure tone testing may be generated by using the one or more processors 30.

Figure 3:
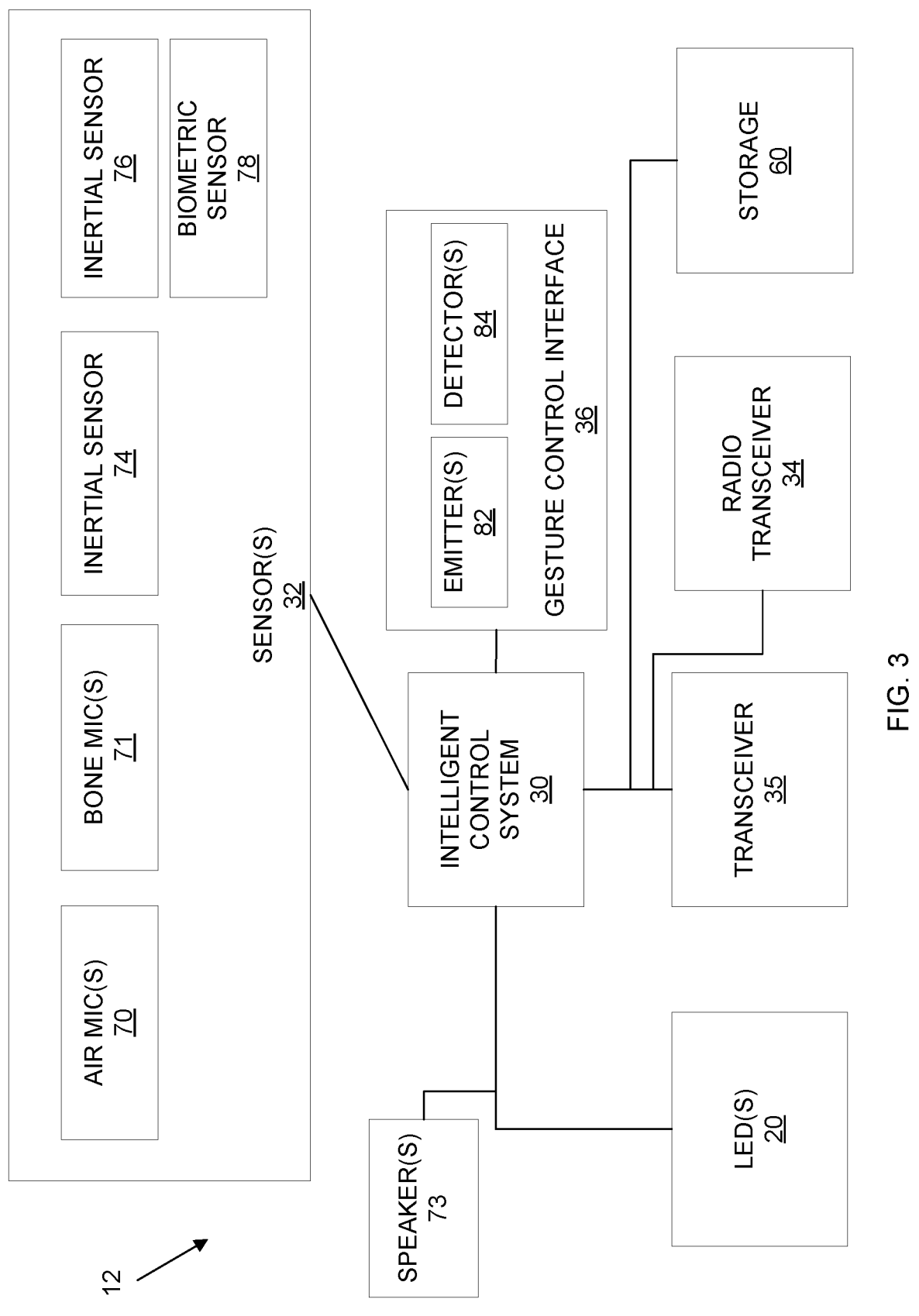
FIG. 3 is another block diagram of an earpiece configured for audiometric testing.
Figure 4:
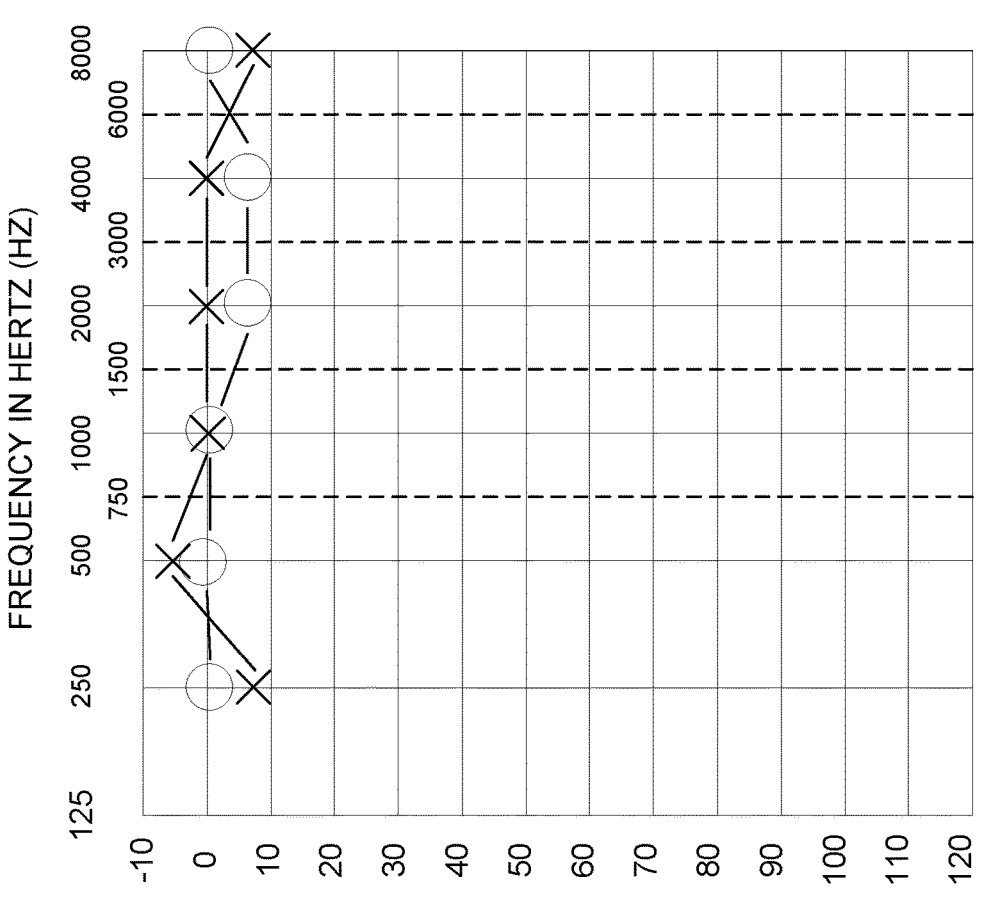
FIG. 4 illustrates another example of an audiogram containing hearing data collected with a wireless earpiece.

FIG. 3 illustrates another example of a block diagram for an earpiece 12 in additional detail. As shown in FIG. 3, various sensors 32 may be operatively connected to the intelligent control system 30. The sensors may include one or more air microphones 70, one or more bone microphones 71, one or more inertial sensors 74, 76, and one or more biometric sensors 78. A gesture control user interface 36 is shown which is operatively connected to the intelligent control system 30. The gesture control interface 36 may include one or more emitters 82 and one or more detectors 84 that are used for receiving different gestures from a user as user input. Example of such gestures may include taps, double taps, tap and holds, swipes, and other gestures. Of course other types of user input may be provided including voice input through one or more of the microphones 70, 71 or user input through manual inputs such as buttons. As shown in FIG. 3, one or more LEDs 20 may be operatively connected to the intelligent control system 30 such as to provide visual feedback to a user. In addition, a transceiver 35 may be operatively connected to the intelligent control system 30 and allow for communication between the wireless earpiece 12 and another earpiece. The transceiver 35 may be a near field magnetic induction (NFMI) transceiver or other type of receiver such as, without limitation, a Bluetooth, ultra-wideband (UWB). A radio transceiver 34 may be present which is operatively connected to the intelligent control system 30. The radio transceiver 34 may, for example, be a Bluetooth transceiver, an UWB transceiver, Wi-Fi, frequency modulation (FM), or other type of transceiver to allow for wireless communication between the earpiece 12 and other types of computing devices such as desktop computers, laptop computers, tablets, smart phones, vehicles, or other devices. The storage 60 may be operatively connected to the intelligent control system 30 to allow for storage including of audio files or programs used in the audio testing and/or results of the audio testing.

According to one aspect, a pure tone audiometry test is performed using a set of wireless earpieces. Such a test may be used to measure the softest or least audible sound that an individual can hear at different frequencies. The loudness or intensity of the sound is measured in decibel (dB), or as previously mentioned may be measured in decibel Hearing Level (dBHL) to represent a variance between a measured hearing level and an average normal hearing level. The tone of the sound (frequency) may be measured in Hertz. In one example of a pure tone audiometry test a sound is produced at one or both ears of an individual which the individual may or may not be able to hear. Test sounds may be generated according to various standards such as ISO-389-7.2005, hereby incorporated by reference in its entirety. The individual provides user feedback regarding whether or not the sound was heard. Thus, feedback is provided from the user.

The earpiece is configured to administer the test to a user. For example, the earpiece may store a plurality of different tones (e.g. different audio files) or be configured to reproduce those tones under programmatic control such as through use of a signal processor. The earpiece is configured to generate the tones, collect user responses, and store the user responses as audiometric test data which may be used to generate an audiogram or for other purposes. In one embodiment, each earpiece includes an air conduction speaker, an air microphone, and a bone conduction transducer which may be a bone conduction microphone which is capable of generating vibration at desired frequencies.

In performing a pure tone test to generate an audiogram the ears may be separately tested. The following levels of testing may be provided: pure tone air, pure tone bone, masked air and masked bone. The pure tone tests for air conduction may be presented to the left and to the right ear individually by the speaker of the respective earpiece device for the test ear at the precise dB output levels required to test the frequency. The masking tones may be provided to an opposite ear for masked air and masked bone response levels.

The bone response levels may be performed in various ways. For example, a bone microphone which is back driven or other transducer is used essentially as a bone vibration speaker for test purposes. Preferably sufficient power is provided so that the transducer may be driven at up to an 80 decibel level.

Where there is hearing loss, it is advantageous to perform bone conduction testing in addition to air conduction testing. This assists in determining where the hearing loss is caused by a sensory issue (sensorineural hearing loss) or a mechanical issue (conductive hearing loss). The bone conduction testing provides for the test to bypass the mechanical parts of the middle ear. Generally, if hearing is better under bone conduction testing than air conduction testing this suggests a conductive hearing loss. Where an individual has hearing loss, performing bone conduction testing with masking (addition of sound at the other ear) prevents sounds from the ear under test from being communicated over to the other ear.

Air Conduction Testing

For air conduction testing with a user under test having a left earpiece and a right earpiece, the air conduction speaker of the right earpiece is used on the right side and the air conduction speaker of the left earpiece is used on the left side. Each set of tones may be performed separately. The tones may be generated by a processor of the earpiece or may be generated by playing one or more audio files stored on one or both of the earpieces.

Masked Air Conduction Testing

For masked air conduction testing, when testing the right ear using the right earpiece, the air conduction speaker of the right earpiece may be used to deliver a pure tone to the right ear. While the pure tone is delivered to the right ear, the air conduction speaker of the left earpiece may be used for masking on the left side for the left ear, thus yielding the masked air level for the right. The opposite is used for testing of the left side, i.e. pure tones are delivered for the left ear by the left speaker, with the masking is provided for the right ear by its air conduction speaker. The masking described provides for additional isolation of the ear under test to avoid any effects of sound reproduced at one ear being heard at the opposite ear.

Bone Conduction

The right earpiece may use the bone microphone or other transducer to drive a bone signal to the right ear, unmasked. Similarly, the left earpiece may use its bone microphone or other transducer to drive a bone signal to the left ear, unmasked.

Masked Bone Conduction Testing

The right earpiece may use the bone microphone of the right ear with the air microphone of the left side used to provide the masking air to block inputs from air conduction into the contralateral ear. For the left earpiece, the bone microphone of the left ear serves as the driver for the masked bone levels, with the air conduction masking provided by the air conduction speaker of the right ear. The masking described provides for additional isolation of the ear under test to avoid any effects of sound reproduced at one ear being heard at the opposite ear. Of course, a similar methodology would be employed for testing of the contralateral ear.

Speech Testing

Another type of audiological testing that may be performed with the earpiece is speech reception threshold testing and/or speech discrimination testing. Tests of listening and speech may be recorded on an audiogram. One example of such a test is the speech reception threshold (SRT). This type of testing may be used to further confirm the results of a pure-tone test. The SRT may be used to determine the least intense (quietest) speech that an individual can hear half the time. Word recognition may be used to determine if the individual can correctly repeat back the words. The SRT may be performed in a quiet environment. Alternatively, the SRT may be performed in an environment where ambient noise is present. Where ambient noise is present, the earpieces may control the amount of ambient noise present or measure the amount of ambient noise present to provide additional information regarding the test including characterizations of the ambient noise.

Another type of testing that may occur is determination of a speech discrimination score. A speech discrimination score (SD) relates to a procedure for determining an individual's ability to identify words (not only hear them). Under this procedure a series of 50 monosyllabic words are presented and a determination is made as to how many of these words (a percentage) that the individual correctly identified. For this test, an earpiece may present the monosyllabic words either through speech processing or playing recorded audio files for the words and then may analyze any response from a user to determine whether the individual correctly identified the word, incorrectly identifies the word or is otherwise unable to determine the word presented.

Yet another type of testing is complex speech tests. This type of testing may be used for various purposes including to evaluate central auditory processing (CAP). One way this type of testing may be implemented is to present one word to the left ear and simultaneously presenting another word to the right ear and receiving user input in the form of the individual repeating both word. The inability to repeat one of the words may indicate a temporal lobe issue.

Otoacoustic Emissions

Another type of testing involves otoacoustic emissions. Otoacoustic emissions are sounds emitted from the ear. These sounds may be detected with one or more microphones of the earpiece positioned within the external auditory canal. The earpieces may acquire these sounds in various manners. For example, these sounds may be regularly or periodically detected without stimulus. Alternatively, these sounds may be evoked in response to a stimulus such as a pure tone. The relationship observed between the pure tone produced and the frequency of the otoacoustic emissions may be used to determine hearing loss.

Acoustic Reflex Threshold

The acoustic reflex is an involuntary muscle contraction of the stapedius muscle in the middle ear that occurs in response to high-intensity sound stimuli or when the person starts to vocalize. The acoustic reflex threshold (ART) is the sound pressure level (SPL) from which a sound stimuli with a given frequency will trigger the acoustic reflex. Where an individual has conductive hearing loss they will have a higher acoustic reflex threshold.

The earpieces may be configured to determine the acoustic reflex threshold. One or more sensors may be used to determine when this occurs. The sensors may include one or more transducers such as bone microphones or air microphones. The earpieces may be used to generate the high-intensity sound stimulus using one or more speakers or other transducers.

Acoustic Reflex Decay Test

In the acoustic reflex decay test a stimulus may be given in the form of a pure tone having a frequency at least 10 dB above the range of the acoustic reflex. This tone may be played for a duration of about 10 seconds. If the muscles are functioning normally, the muscles contract and stay contracted for the full duration of the tone. The earpieces may be used to emit the tone and monitor the state of the muscle contractions in order to administer the test.

Calibration

As an optional initial step, the earpiece may perform self-calibration. This may occur in various ways. For example, the earpiece may emit a sound from its own speaker and detect the sound using one or more of its own microphones. The earpiece may then calibrate the intensity of the sound emitted to the intensity of the sound detected and/or the frequency of the sound emitted to the frequency of the sound detected. In this way, the earpieces may be accurate and precise in the levels of sound they produce.

Responsive Testing

According to another aspect, the occurrence of testing may be in response to actual conditions. For example, the earpieces may be used to monitor environmental sounds, listen for, and detect extremely loud noises which have the potential to have an adverse effect on hearing. In such instances, the earpieces may be used to record the dB level of the tones or sounds, the frequency or frequencies, the length of time of noise exposure or other characteristics of the sound. Where the frequencies of the sounds exceed a threshold, the earpiece may alert the user that they should move from the area based on the measurement parameters and may communicate these parameters to the user directly or indirectly (such as through an app running on a mobile device). In addition, other sensor data may be collected including temperature data or humidity data. After detection of lowered levels of audiometric challenges to the external ear, testing may be performed to validate the presence or absence of temporary threshold shifts.

Workplace Testing

Where individuals are exposed to loud noises as a part of their work environment, this continuous and daily exposure can have an adverse effect on their hearing. Where the earpieces are worn at work, not only can the presence of the earpieces serve a protective function for workers by isolating them from direct ambient sound, but the earpieces may also record the noise levels which may lead to noise-induced permanent threshold shifts in the hearing of workers who are not protected by the earpieces.

User Interaction

According to another aspect, relates to how the earpieces interact with and respond to a user. For example, a user may indicate whether or not they hear a tone by providing an audio response. The audio response may be in response to a prompt of the earpieces. For example, the earpieces may ask the user "Did you hear the tone in your right [left] ear?" and ask for a response. The user may respond in various ways. For example, the user may respond through voice feedback such as by specifying "Yes" or "No" or "I don't know" or "I am not sure." Another way that the user may respond is through head movement where the earpiece includes one or more inertial sensors. Thus, in response to a prompt from the earpieces, the user may nod their head up and down to indicate a "yes" or may move their head with side to side movement to indicate a "no."

Another way that the user may respond is through touching a button or surface on the earpiece. Where a surface provides a gestural interface, a tap may indicate yes, a swipe may indicate "no" or taps, double taps, triple taps, tap and holds, or different types of swipes may be used to communicate a response from a user. Note that in these various examples, the test may be administered without the use of a screen display. If a screen display is used, the screen display may be associated with a computer, mobile device, smart glasses or other device.

Once data associated with the test is collected it may be used in various ways. In one example, the data is communicated to another device which may then display the data. For instance, the data associated with an audiogram may be communicated to a mobile app executing on a mobile device such as a smartphone or tablet. Of course, other types of computing devices may be used. The software on the device may perform a number of different functions. For example, it may generate a display of an audiogram based on the data received. It may also provide for analysis. For example, the software may characterize results of testing relative to normal hearing or relative to previous tests. It may characterize results of the left ear relative to the right ear. By way of further example, the software may combine data from multiple tests and perform an analysis to interpret the data to determine a type of hearing loss present or to characterize or quantify the hearing loss or the progression of hearing loss over time. In a further example, the software may provide for determining modifications in how environmental sounds are processed by and reproduced by the earpiece and communicating those modifications to the earpieces. The software may recommend that the user see a medical professional and may provide for communicating the results of the test to the medical professional. The software may perform for other and additional functionality relating to collection, analysis, and use of the data.

In some tests, for example in otoacoustic emissions testing and acoustic reflex testing, the user feedback is determined directly from sounds emitted by the user or muscle feedback from the user. Thus, in certain types of testing, the user need not provide any additional feedback.

Tinnitus Frequency Matching

According to another aspect tinnitus frequency matching may be performed. In this mode of operation, tones are presented to the user and the user may then confirm when a tone presented matches the perceived tone of the tinnitus experienced by the user. This could be used for removal of the involved frequency from an audio signal of the device in all aspects including phone calls, recorded or streamed music, or processed environmental sounds. Thus, by knowing the frequency of the tinnitus, audio processing may be performed to subtract, attenuate, or otherwise modify this aspect of a user's hearing profile into consideration in order to produce an improved experience.

Passive or Background Testing

Because the earpieces described are multi-function and may be used by individuals in any number of different situations in daily life including while exercising, to talk on the phone, while listening to music, or otherwise, additional benefits are provided. In particular, the earpieces may have testing modes that may work in the background to evaluate the hearing of a user on an ongoing basis or to make observations which would be indicative that a user should perform hearing tests. For example, the earpieces may determine intensity levels of ambient noise over time. Where these levels are above a threshold, the earpieces may suggest that the user undergoing a series of hearing tests because there may be a greater likelihood of hearing loss. Where a user consistently maintains a high volume setting associated with the earpieces or audio from other sources, the earpiece may suggest that the user undergoing a series of hearing tests. The earpiece may otherwise identify particular patterns in usage of the earpieces which may be indicative of a loss of hearing and then suggest hearing tests be performed.

Customization

According to another aspect, a customized solution may be provided to address issues that a person experiences. For example, if there was a high tone loss, compression algorithms and gains may be applied as appropriate to provide a custom experience for each of the users. Thus, the earpieces described therein may provide for improved audio processing. These improvements to audio processing may be implemented across any number of different modalities which may be used by the earpiece(s). For example, where the earpieces are configured to reproduce environmental sounds the earpieces may provide for processing to compensate for hearing loss. Where the earpieces are configured for telephone calls, the earpieces may provide for processing to compensate for hearing loss. Note that for phone calls the frequency range may be less than the full range of hearing and so different algorithms may be used for phone call specific audio as opposed to environment audio. Incoming media may also be manipulated based on the hearing of user. This may include streaming audio from smart phones, televisions, computers, or other devices. In each of these cases, the earpieces may adjust and respond to the parameters determined by the audiometric testing provided by the earpieces. Thus soundscapes for an individual may be customized based on individual preferences including an individual's hearing as determined by tests performed by the earpiece itself as well as by the type of audio (e.g. environmental sound, phone call, streaming audio from other devices). Thus, audio profiles associated with a user may be modified based on results of audiometric testing data. The audio profiles for the user may be stored on one or more of the earpieces.

Information collected may also be communicated to an individual to their health care provider(s) to assist in management of the individual's health care and provide a rich data set which will assist in effective and efficient diagnostics and treatment of the individual.

Therefore, improved wireless earpieces have been shown and described that include built-in features for audiometric testing. In addition, associated methodology is provided for administering audiometric tests with earpieces, reporting the results of the audiometric tests, and using the results of the audiometric tests to determine how to modify audio heard by a user. Although specific embodiments have been shown and described herein, the present invention contemplates numerous options, variations, and additions, including combinations of various embodiments shown and described.

What is claimed is:

1. A method for performing audiometric testing by a wireless earpiece sized and shaped to fit into an external auditory canal of a person, the method comprising steps of:

performing audiometric testing based on an otoacoustic emissions test by generating a sound at a speaker of the wireless earpiece while the speaker is within the external auditory canal of the person and receiving a frequency of otoacoustic emissions feedback at a microphone of the wireless earpiece, wherein the microphone is within the external auditory canal of the person; and generating audiometric data characterizing hearing of the person based on characteristics of the sound and feedback of the person, and based on characteristics of the sound generated during the otoacoustic emissions test and a frequency of the otoacoustic emissions feedback, and based on testing modes working in a background to evaluate hearing of the person on an ongoing basis, wherein generating the audiometric data is performed by the wireless earpiece;

communicating the audiometric data from the wireless earpiece to a computing device in wireless communication with the wireless earpiece;

displaying an audiogram on the computing device, wherein the audiogram illustrates an audible threshold for different standardized frequencies, with frequency measured in Hertz on an x-axis and intensity measured in decibel on a y-axis, wherein the threshold is plotted against a standardized curve associated with normal hearing;

receiving an audio signal at the wireless earpiece;

modifying the audio signal to accommodate the person based on the audiometric data characterizing the hearing of the person and using different algorithms adjusted and intelligently responsive to parameters determined by the audiometric testing data generated by the earpiece, for different types of audio to provide a modified audio signal, the modifying performed by the wireless earpiece; and transducing the modified audio signal at the speaker of the wireless earpiece while the speaker is within the external auditory canal of the person;

wherein the type of the audio is one of a phone call audio, environmental sound, and streaming audio.

2. The method of claim 1 wherein the sound is a pure tone sound.

3. The method of claim 1 further comprising modifying an audio profile associated with the person under test based on the audiometric data, the modifying performed by the wireless earpiece, wherein the audio profile is stored on the wireless earpiece.

4. The method of claim 3 wherein the modifying an audio signal is performed using the audio profile of the person.

5. A method for performing audiometric testing by a wireless earpiece sized and shaped to fit into an external auditory canal of a person, the method comprising steps of:

performing audiometric testing of a person, by the wireless earpiece wherein the wireless earpiece is within a set of wireless earpieces, by reproducing sounds with at least one transducer of a left earpiece and at least one transducer of a right earpiece and receiving user feedback regarding the sounds to provide audiometric test data at the set of earpieces;

performing audiometric testing characterizing hearing of the person, comprising an otoacoustic emissions test by generating a sound at a speaker of the wireless earpiece while the speaker is within the external auditory canal of the person and receiving a frequency of otoacoustic emissions feedback at the wireless earpiece at a microphone of the wireless earpiece positioned within the external auditory canal of the person;

monitoring environmental sounds;

implementing responsive testing at the wireless earpiece, when the monitoring of environmental sounds detects sounds with a potential to have an adverse effect on hearing of the person;

alerting the person with results of the responsive testing;

generating audiometric data characterizing hearing of the person, the audiometric data comprising characteristics of the sound at the speaker and the feedback at a processor of the wireless earpiece from the otoacoustic emissions test;

communicating the audiometric data from the wireless earpiece to a computing device by a wireless transceiver of the wireless earpiece;

displaying to the person with the wireless earpiece, an audiogram on the computing device, wherein the audiogram illustrates an audible threshold for different standardized frequencies, with frequency measured in Hertz on an x-axis and intensity measured in decibel on a y-axis, wherein the threshold is plotted against a standardized curve associated with normal hearing;

receiving an audio signal at the wireless earpiece, wherein the wireless earpiece is within the set of wireless earpieces with the audiometric test data at the set of earpieces and the wireless transceiver communicates with another wireless earpiece within the set of wireless earpieces;

modifying the audio signal based on the audiometric data characterizing the hearing of the person and a type of the audio signal, the modifying performed by at least one of the wireless earpieces;

transducing the modified audio signal at the speaker of at least one of the wireless earpieces while the speaker is within the external auditory canal of the person; and wherein the type of the audio signal is one of a phone call audio, environmental sound, and streaming audio.

6. The method of claim 5, wherein the microphone comprises an air conduction microphone.

7. The method of claim 6, wherein the microphone further comprises a bone conduction microphone appropriately positioned.

8. The method of claim 5, further comprising: calibrating at least one of an intensity of a calibration sound emitted from the speaker to an intensity of a sound detected at the microphone, and a frequency of the calibration sound emitted from the speaker to a frequency of the sound detected at the microphone by at least one of the wireless earpieces within the set of wireless earpieces.

9. The method of claim 5, wherein the wireless transceiver is a Bluetooth transceiver.

10. A method for performing audiometric testing by a wireless earpiece sized and shaped to fit into an external auditory canal of a person, the method comprising steps of:

emitting a calibration sound with an intensity and frequency from a speaker of the wireless earpiece while the speaker is within the external auditory canal of the person;

receiving a sound at a microphone of the wireless earpiece in response to the emitting of the calibration sound;

calibrating at least one of the intensity of the calibration sound emitted to an intensity of the sound detected at the microphone of the wireless earpiece within the external auditory canal of the person, and the frequency of the calibration sound emitted to a frequency of the sound detected at the microphone of the wireless earpiece within the external auditory canal of the person;

performing an otoacoustic emissions test by generating a sound at the speaker of the wireless earpiece while the speaker is within the external auditory canal of the person and receiving otoacoustic emissions feedback at the wireless earpiece from at least one microphone within the external auditory canal of the person; and generating audiometric data characterizing hearing of the person based on characteristics of the sound and a frequency of the feedback, wherein the generating the audiometric data is performed by the wireless earpiece;

monitoring environmental sounds;

implementing responsive testing at the wireless earpiece, when the monitoring of environmental sounds detects sounds with a potential to have an adverse effect on hearing of the person;

alerting the person with results of the responsive testing;

modifying an audio profile by the wireless earpiece, the audio profile associated with the person under test based on the audiometric data, wherein the audiometric data is characterizing hearing of the person based on characteristics of the sound and a frequency, and of the feedback and ongoing background testing modes to evaluate hearing of the person, such audio profile is stored on the wireless earpiece;

receiving an audio signal at the wireless earpiece;

modifying the audio signal with processing parameters based on type of audio, wherein the audio signal is processed using frequency settings associated with characteristics of the audio type and the audio profile associated with the person to provide a modified audio signal; and transducing the modified audio signal at the speaker of the wireless earpiece while the speaker is within the external auditory canal of the person;

wherein the type of the audio is one of a phone call audio, environmental sound, and streaming audio.

11. The method of claim 10 wherein the sound is a pure tone sound.

12. The method of claim 10 wherein the wireless earpiece is within a set of wireless earpieces, and a transceiver communicates with another wireless earpiece within the set of wireless earpieces and the audio profiles are stored on one or more of the wireless earpieces.

\* \* \* \* \*